United States Patent [19]

D'Alo et al.

[11] 4,326,519
[45] Apr. 27, 1982

[54] VENIPUNCTURE DEVICE

[75] Inventors: Herbert F. D'Alo, Crystal Lake; Andrew J. Muetterties, Gages Lake, both of Ill.

[73] Assignee: Abbott Laboratories, North Chicago, Ill.

[21] Appl. No.: 123,522

[22] Filed: Feb. 21, 1980

[51] Int. Cl.³ .................... A61M 5/00; A61M 25/00
[52] U.S. Cl. ............................ 128/214.4; 128/221; 128/DIG. 16
[58] Field of Search ........... 128/214 R, 214.4, 214.2, 128/221, 348, DIG. 16, DIG. 26

[56] References Cited

U.S. PATENT DOCUMENTS

| | | | |
|---|---|---|---|
| 3,399,674 | 9/1968 | Pannier et al. | 128/221 X |
| 3,651,807 | 3/1972 | Huggins | 128/214.4 |
| 3,766,916 | 10/1973 | Moorehead et al. | 128/214.4 |
| 4,037,600 | 7/1977 | Poncy et al. | 128/DIG. 16 X |
| 4,137,916 | 2/1979 | Killman et al. | 128/214.4 |
| 4,170,993 | 10/1979 | Alvarez | 128/214 R |
| 4,194,504 | 3/1980 | Harms et al. | 128/214.4 |

Primary Examiner—Gene Mancene
Attorney, Agent, or Firm—Robert L. Niblack; Robert S. Beiser

[57] ABSTRACT

An improved venipuncture device comprises a catheter having a catheter hub at one end, with a needle having a needle hub at one end and a sharpened tip at the second end extending through the catheter and catheter hub. The needle is adapted for insertion and removal from the catheter. A fin extends substantially vertically from the needle hub and is constructed and arranged for gripping the device in a manner which facilitates venipuncture.

13 Claims, 6 Drawing Figures

VENIPUNCTURE DEVICE

BACKGROUND OF THE INVENTION

The present invention relates generally to venipuncture devices and more particularly to an easily separable over-the-needle catheter insertion device.

Catheter insertion devices are widely available in the prior art. However, the hospital products industry continuously strives to improve such devices in an attempt to provide simpler, easier to use, disposable devices than are presently on the market. Several specific areas of endeavor have been pursued, such as providing an easily operable means of connecting the catheter hub to the needle hub so as to join the two during insertion, but allow quick release when desired. Similarly, various designs have been put forward for gripping the device during venipuncture in order to facilitate the ease of such an operation.

The following U.S. patents describe devices developed to address these problems:

U.S. Pat. No. 4,137,916 "Catheter Plug Assembly", Don M. Killman, et al., issued Feb. 6, 1979.

U.S. Pat. No. 3,714,945 "Digit Manipulable Quick-Release Cannula Insertion Device", Vaden F. Stanley, issued Feb. 6, 1973.

U.S. Pat. No. 3,595,230 "Intravenous Catheter Placement Unit with Tubular Guide Sheath", George M. Suyeoka, et al., issued Jan. 27, 1971.

U.S. Pat. No. 3,589,361, "Intravenous Catheter Unit with Flexible Wing Support and Inserter Means", Douglas A. Loper, et al., issued June 29, 1971.

U.S. Pat. No. 3,584,625, "Detachable Guide Needle", Edwin Grant Swick, issued June 15, 1971.

U.S. Pat. No. 3,537,451, "Intravenous Catheter Unit with Releasable Inserter Means", Dale F. Beck et al., issued Nov. 3, 1970.

U.S. Pat. No. 3,359,978, "Guide Needle for Flexible Catheters", R. M. Smith, Jr., issued Dec. 27, 1967.

U.S. Pat. No. 3,161,197, "Catheter", W. W. Glas, et al., issued Dec. 15, 1964.

U.S. Pat. No. 3,064,648, "Intravenous Needle Assembly", A. F. Bujan, issued Nov. 20, 1962.

The above-listed devices have met with varying degrees of success. Accordingly, it is an advantage of the present invention to provide an improved venipuncture device which may easily be gripped from above during insertion of the device into the patient's vein. It is an additional advantage of the present invention over the prior art to provide a venipuncture device in which the needle may be easily separated from the catheter after venipuncture has occurred, using either the single-handed or double-handed method. It is a further advantage of the invention to provide an improved venipuncture device which locks the catheter and needle hub assembly together during venipuncture, but which is easily releasable when desired.

SUMMARY OF THE INVENTION

The present invention is an improved venipuncture device comprising a catheter having a catheter hub attached at one end, and a needle having a needle hub attached at one end with a sharpened tip at its second end. The needle extends coaxially through the catheter with its sharpened tip extending from the catheter. A fin extends substantially vertically from the needle hub and is precisely positioned and sized so as to allow the device to be gripped from above and easily controlled during venipuncture.

The fin member is designed to best allow manipulation of the device during venipuncture. One means by which this is accomplished is by having the fin extend longitudinally from the needle hub along the catheter hub for a substantial portion of the length of the catheter hub in order to move the gripping point towards the tip of the device thereby shortening the movement arm and facilitating manipulation and control of the device during venipuncture. Along these same lines, the base of the fin is disposed as closely as possible to the center line of the device, and is adapted for gripping, thereby further facilitating manipulation.

An additional means for easily grasping and manipulating the fin is by including a pair of surfaces extending substantially along the fin on each side. The surfaces are large enough and close enough together to be easily grasped between the thumb and index finger of the user. As a result, the device may be easily picked up and held during venipuncture. Along these same lines a series of ribs may be integrally formed in the fin. These ribs strengthen the fin for purposes of rigidity during venipuncture and at the same time improve the gripability of the surface.

An additional feature of the fin member is the construction of the upper surface of the fin member in a substantially horizontal configuration. The horizontal configuration of this upper surface as well as the spacial arrangement to the bottom of the needle hub permits the device to be easily grasped from above and below. As a result, of all of these features, the user has greater tactile sensation, or kinesthesis (perception of the position of the needle), when utilizing the device.

A feature of the invention is the use of a guide track mechanism longitudinally disposed along the catheter hub and needle hub which allows slidable attachment or detachment of the needle hub and catheter hub. The guide track mechanism also prevents rotation of the needle within the catheter during venipuncture. In a preferred embodiment, the fin extends vertically from the guide track. This allows the fin to be used in conjunction with the guide track in order to join or separate the two hubs.

In a preferred embodiment the guide track mechanism comprises a substantially T-shaped track extending coaxially along the catheter hub. A substantially rectangular female track member extends proximally from the needle hub and has an open lower portion and an aperture through it constructed and arranged for telescopic reception and snub gitting attachment to the male track, so as to join the catheter and the needle hub together. Other track configurations may also be used.

In regard to maintaining the position of catheter after venipuncture, as well as inserting it during venipuncture, an additional feature of the invention is the use of a pair of oppositely extending flexible wing sections attached to the catheter hub. Each wing may have an area of reduced thickness along a portion of the width adjacent to the catheter hub. This area of reduced thickness facilitates folding of the flexible wing sections together so that they may easily be held between the thumb and index finger of the user during venipuncture, or to hold the catheter hub in position while removing the needle hub. However, the wings are designed primarily for taping down after venipuncture. The wings may be flexibly attached to a wing hub member which is telescopically received by the catheter or attached directly to the catheter hub. The forward surface of the fin is spaced sufficiently from the wings and is of sufficient height and width so that the device may be held by the flexible wings and a single finger pressed against the forward surface of the fin, thereby separating the needle hub and needle from the catheter and catheter hub. However, in a preferred embodiment, a raised tab member extends from the wing hub or catheter hub. The index finger is pressed against this raised tab, while holding the fin between the thumb and middle finger, to separate the needle hub and catheter hub. The needle hub and catheter hub may be separated after the initial entry of the needle during venipuncture, after the needle is fully inserted or at any point in between.

An additional feature of the invention is the use of an additive port extending radially from the catheter hub and adapted for joinder with a length of flexible tubing. Utilizing this additive tubing port, blood may be removed from the device through the port or through a reseal member positioned within the catheter hub. Alternatively, the additive tubing port may be used to preprime the device using a priming aperture integrally formed in the needle. When the needle is fully extended in the catheter, the priming aperture is positioned proximate to the tubing port. Liquid may be introduced through the flexible tubing, into and through the additive tubing port, into and through the priming aperture and into and through the needle so as to fill the needle with solution and thereby prevent the passage of air bubbles into the vein of the patient. In order to prevent the presence of such air bubbles or contamination of the device, a penetrable elastic sealing member is preferably positioned within the catheter hub so that the needle may extend coaxially therethrough the catheter hub and catheter while retaining a hermetic seal of the device. In addition, the needle may be inserted or removed without contaminating the device.

In an alternative embodiment of the invention, the previously mentioned catheter device utilizes a guide track mechanism without the use of a fin member between the needle hub and catheter hub for slidable attachment or detachment of each to the other. In addition, the use of a guide track again prevents rotation of the needle within the catheter during venipuncture. While this embodiment does not utilize the previously mentioned fin member, the catheter hub and needle hub may nevertheless be easily separated or joined as desired.

DETAILED DESCRIPTION OF THE PREFERRED EMBODIMENT

Figure 1:
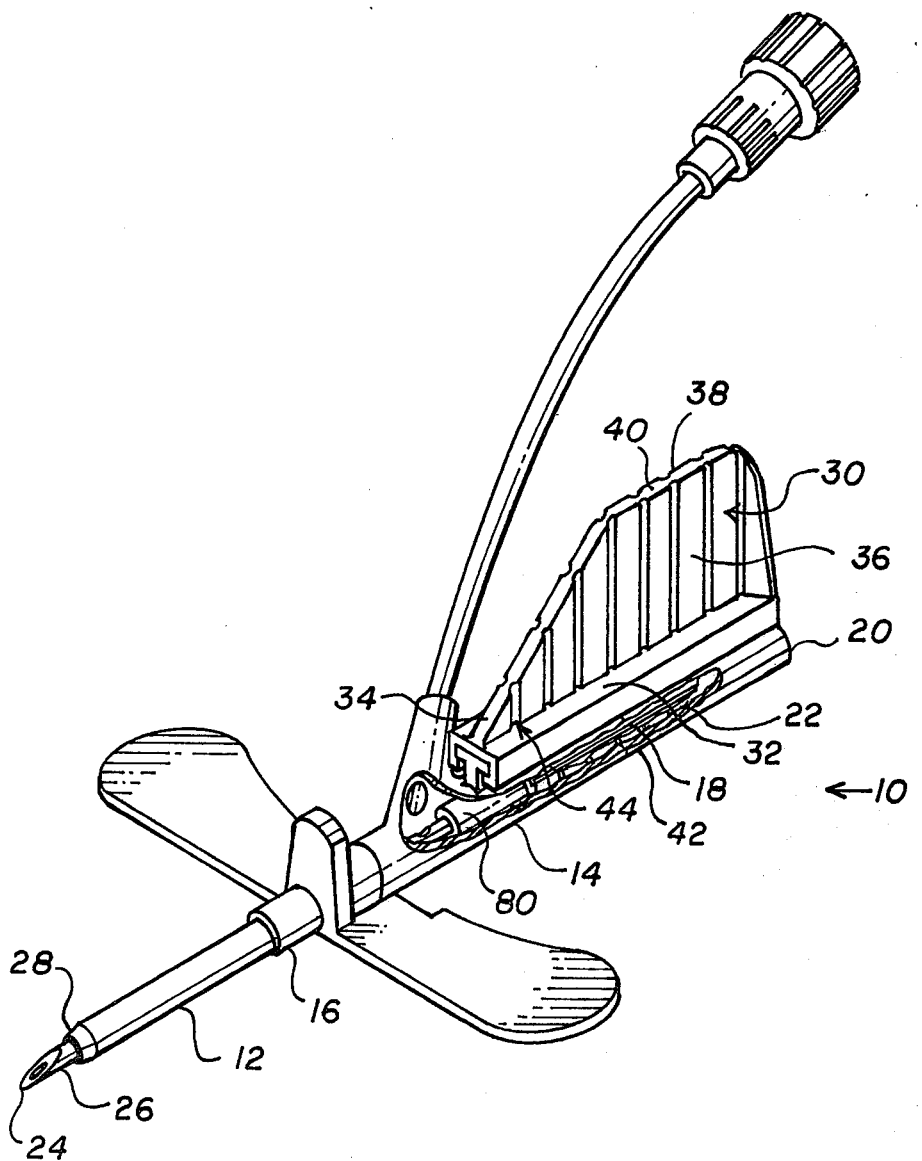
FIG. 1 of the drawings is a front perspective view, partially broken away, of an improved venipuncture device.

While this invention is susceptible of embodiment in many different forms, there will be shown in the drawings and will herein be described in detail, several specific embodiments, with the understanding that the present disclosure is to be considered as an exemplification of the principles of the invention and is not to limit the invention to the embodiments illustrated.

As seen in FIG. 1, improved venipuncture device 10 comprises a catheter 12 having a catheter hub 14 attached thereto at first end 16. A needle 18 having a needle hub 20 attached thereto at first end 22 and sharpened tip 24 at second end 26 extends coaxially through catheter 12, with sharpened tip 24 extending from catheter 12 at second end 28 of catheter 12. Needle 18 is adapted for insertion and removal from catheter 12; it may be slidably introduced or removed. Fin member 30 extends substantially vertically from needle hub 20 and is constructed and arranged for gripping of device 10 in order to facilitate venipuncture.

As further seen in FIG. 1 of the drawings, guide track mechanism 32 extends longitudinally along catheter hub 14 and needle hub 20. Guide track mechanism 32 is constructed and arranged for slidable attachment or detachment of needle hub 20 to catheter hub 14. Guide track mechanism 32 also prevents rotation of needle 18 within catheter 12 during venipuncture. As shown, fin member 30 extends substantially vertically from guide track mechanism 32. Fin member 30 is designed to facilitate joining or separating catheter hub 14 from needle hub 20 by means of guide track mechanism 32; in other words, fin member 30 is used to slide guide track mechanism 32 forward or back.

The design of fin member 30 is particularly adapted for this gripping and separation function. One example is the length of fin member 30. Fin member 30 extends longitudinally from needle hub 20 to a point 34 when needle 18 is fully extended through catheter 12. As a result, device 10 may be gripped more closely to the tip 24 of needle 18 thereby shortening the movement arm of device 10 making it more easily balanced and manipulated during venipuncture. As further seen in FIG. 1, base portion 44 of fin member 30 is disposed as closely as possible to the central axis of needle 12. Substantially planar surfaces 36 and 38 also extend to base 44 of fin 30. As a result, device 10 may be gripped closely proximate to the axis of needle 12, thereby facilitating manipulation of the device 10 during venipuncture. Along these same lines, a key feature of fin member 30 is a design of surfaces 36 and 38. Surfaces 36 and 38 are oppositely disposed on fin member 30. They are substantially vertical and are also at least large enough to be grasped between the thumb and index finger of the user. As a result, surfaces 36 and 38 may be grapsed from above by the thumb and middle finger of the user in order to allow easy use of venipuncture device 10.

An additional feature of fin member 30 is the position and configuration of substantially horizontal upper surface 40. The height of fin member 30 is such that substantially horizontal upper surface 40 is close enough to bottom surface 42 of needle hub 20 to permit gripping of device 10 between the thumb and index finger of the user with the thumb on substantially horizontal surface 40 and the index finger looped below bottom surface 42 of needle hub 20. Thus, a multiplicity of gripping techniques may be utilized with the present device.

Figure 2:
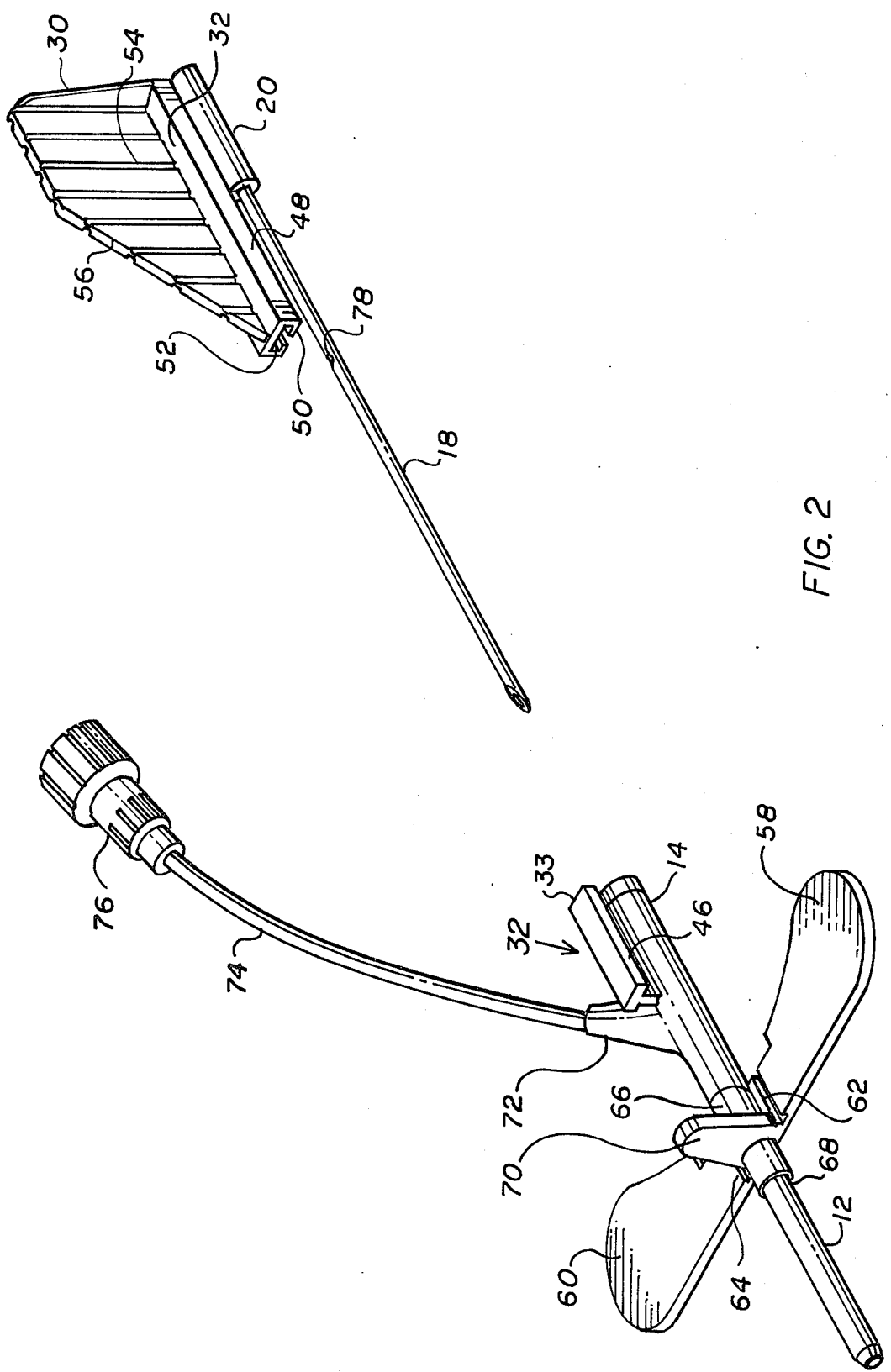
FIG. 2 of the drawings is a front perspective view of the improved venipuncture device of FIG. 1 showing in particular the needle, needle hub and fin members separated from the catheter and catheter hub section of the device.

As best seen in FIG. 2 of the drawings, guide track mechanism 32 comprises a substantially T-shaped male track member 46 extending coaxially along catheter hub 14. A substantially rectangular female track 48 extends forwardly from the proximal portion of needle hub member 20. Female track member 48 has open lower portion 50 and an aperture extending coaxially through it which is constructed and arranged for telescopic reception of male track member 46. In addition, the interior dimensions of aperture 52 are slightly larger than the dimension of T-shaped track member 46. As a result, T-shaped track member 46 snugly fits into aperture 52 so as to attach the two when T-shaped track member 46 is telescopically inserted into aperture 52. Means for attaching needle 20 to catheter hub 14 are thereby provided. However, front to back movement of guide track member 32 during venipuncture is prevented by the abutment of the proximal portion of needle hub 20 to the distal portion of catheter hub 14.

An additional feature of the invention is the inclusion in fin member 30 of a plurality of ribs 54 integrally formed therein. Ribs 54 structurally strengthen fin member 30 so that a minimum of material may be used while at the same time sufficient rigidity is provided for gripping and application of force during venipuncture. In addition, the inclusion of ribs 54 provides a rougher surface for gripping, thereby increasing adhesion during venipuncture.

The preferred means for accomplishing separation of catheter hub 14 from needle hub 20 is through use of tab member 70, which extends from wing hub member 66 substantially vertically. Tab 70 is of sufficient size to allow force to be applied by a single digit against it. As a result, when fin member 30 is grapsed, the index finger may be pressed against tab member 70 and needle hub 20 is consequently separated from catheter hub 14.

Alternatively, in order to separate needle 10 from catheter 12, the middle finger may be pressed backward against surface 56. Fin member 30 and needle hub 20 are thereby moved distally along guide track mechanism 46 until female track member 48 is separated from male track member 46. Fin member 30 may then be grasped by a second hand and needle 18 completely removed from catheter 12 and catheter hub 14. In order to accomplish such separation however, catheter hub 14 must be maintained in a stationary position, either through the use of flexible wings 58 and 60 or by grasping hub 14 itself and maintaining it in that position.

Forward surface 56 of fin member 30 is substantially vertical (approximately 45°-90°) in order to facilitate such digital separation of needle hub 20 from catheter hub 14. By this it is meant that when catheter hub 14 is maintained in a stationary position, needle hub 20 may be moved backwards by pressing a single digit against forward surface 56. As shown in FIG. 2, guide track means 32 connect needle hub 20 to catheter hub 14 and therefore when digital force is applied against forward surface 56, female track member 48 slides distally along male track member 46 until the hubs are separated. However, it is clear that even without the use of a guide track mechanism needle hub 20 and catheter hub 14 could be separated simply by application of force against forward surface 56 of fin member 30. However, grasping of fin member 30 during venipuncture is the preferred method.

An additional feature of venipuncture device 10 is the inclusion of a pair of oppositely extending flexible wing sections 58 and 60 flexibly attached to catheter hub 14. Flexible wing sections 58 and 60 may have an area of reduced thickness 62 and 64 adjacent to catheter hub 14 to facilitate folding of flexible wing sections 58 and 60 together vertically so that they may be easily held between the thumb and index finger of the user, thereby allowing venipuncture to be performed from above device 10. However, grasping of fin member 30 during venipuncture is the preferred method. As shown in FIG. 2, in one embodiment, flexible wings 58 and 60 are flexibly attached to a wing hub 66, which has an axial bore 68 therethrough adapted for telescopic reception of and attachment to catheter 12. The use of such a wing hub allows selection of different materials from that of catheter hub 14, thereby permitting construction of a rigid catheter hub 14 and flexible wings 58 and 60. Of particular interest in the present invention is the use of flexible wings 58 and 60 in conjunction with forward surface 56 of fin member 30. Venipuncture may be accomplished by folding flexible wings 58 and 60 upward and grasping them between the thumb and index finger of the user. However, fin member 30 must also be grasped in order to prevent slippage of needle 18 within catheter 14 during venipuncture. Needle 18 is then used to puncture the skin of the patient and inserted into a vein. Once venipuncture is initially accomplished needle 18 may be removed from catheter 12.

An additional feature of the invention is the inclusion of additive tubing port 72, extending radially from catheter hub 14. Additive tubing port 72 is adapted for connection to a length of flexible tubing 74. In a preferred embodiment, flexible tubing 74 includes a cap 76 which seals flexible tubing 74. Cap 76 may be penetrable using a hypodermic needle, or may simply be a sealed overcap and may be used to introduce medicaments or withdraw blood as required. Alternatively, cap 76 may comprise a female luer lok type connector. In order to properly utilize venipuncture device 10, a priming aperture 78 is integrally formed in needle 18. Priming aperture 78 is positioned on needle 18 so that when needle 18 is fully extended through catheter 12, priming aperture 78 is positioned proximate additive tubing port 72 within catheter hub 14. As a result, an intravenous solution may be introduced into flexible tubing 74, into and through additive tubing port 72, into and through priming aperture 78, and into and through needle 18. Needle 18 is thereby filled with an intravenous solution when venipuncture is performed and the presence of air bubbles in the device which may be injected into the patient is prevented.

Along these same lines, in order to maintain the interior of catheter hub 14 in a sterile condition, in a preferred embodiment, reseal member 80 is positioned in the distal portion of catheter hub 14 as best seen in FIG. 1. Reseal member 80 is constructed of a resilient elastomeric material which is penetrable by needle 18, but which seals itself upon withdrawal of needle 18. Penetrable elastic sealing member 80 is also sufficiently elastic to allow easy penetration of or removal of needle 18.

Figure 3:
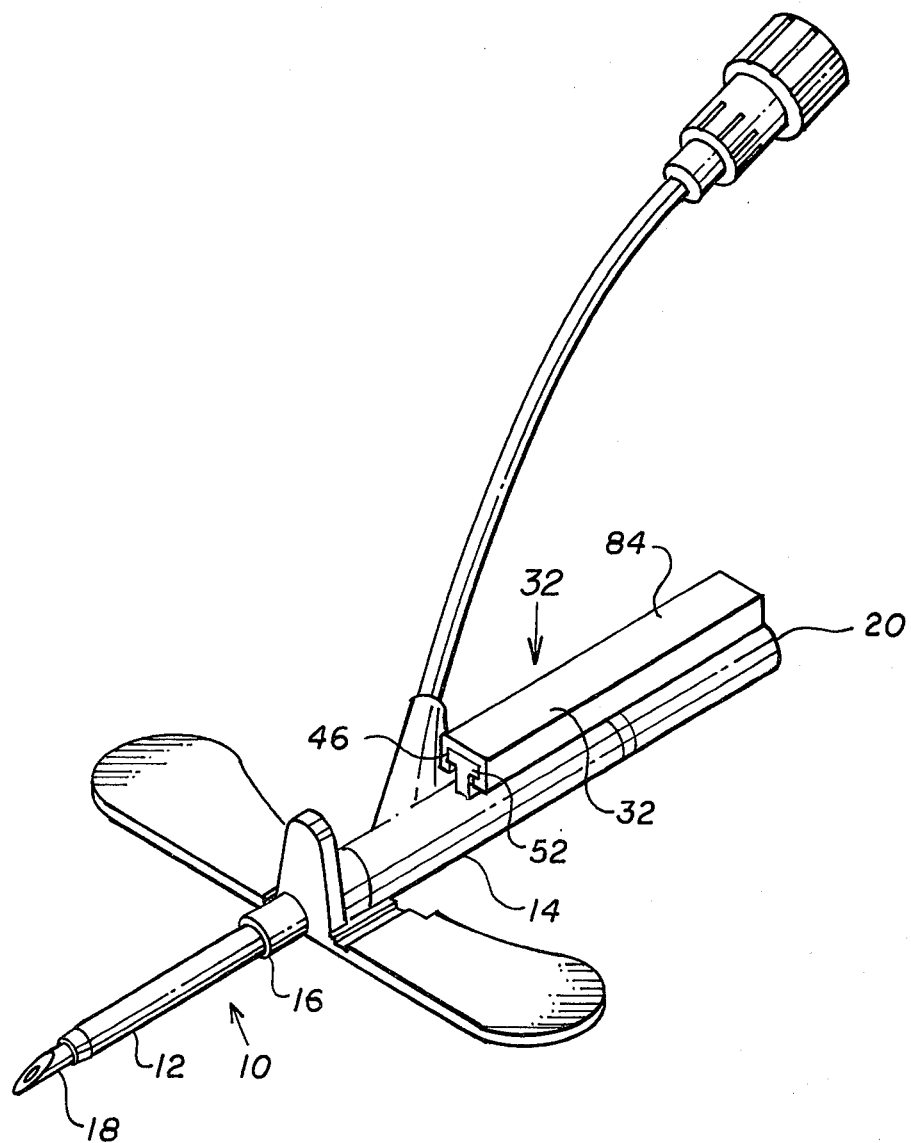
FIG. 3 of the drawings is a front perspective view of an alternative embodiment of an improved venipuncture device.

As best seen in FIG. 3 of the drawings, in an alternative embodiment of the invention, intravenous device 10 again comprises a catheter 12 having a catheter hub 14 attached at first end 16 and a needle 18 attached to a needle hub 20. Needle hub 20 is joined to catheter hub 14 by means of guide track mechanism 32. Again, guide track mechanism 32 comprises male track member 46 disposed along catheter hub 14 and female track member 48 extending proximally from needle hub 20. Female track member 48 includes aperture 52 for telescopic reception of and snug fitting attachment to male track member 46. In the embodiment shown, however, fin member 30 is noticeably absent. Needle hub 20 may be separated from catheter hub 14 by grasping needle hub 20 and slidably removing it by means of guide track mechanism 32.

Figure 4:
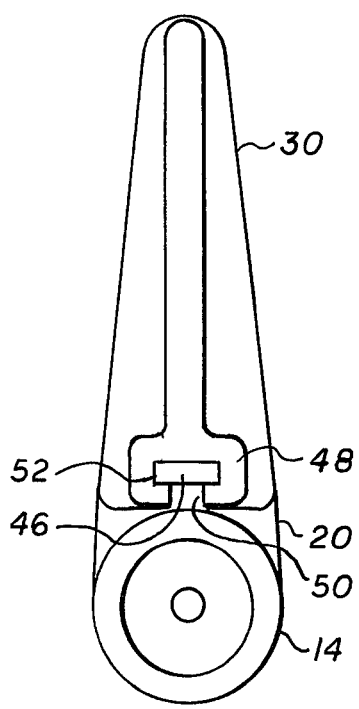
FIG. 4 of the drawings is a front view of the needle hub and fin member of FIG. 1 showing in particular a guide track mechanism integrally formed in the needle hub.
Figure 6:
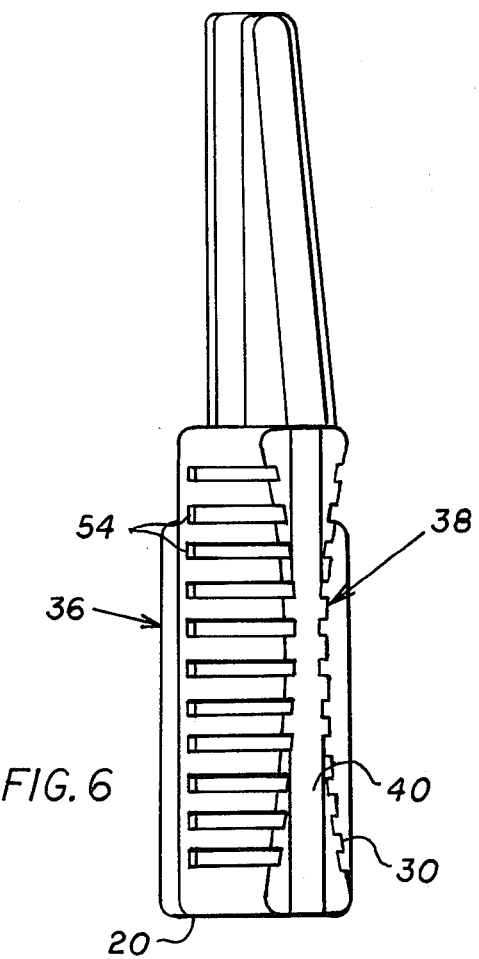
FIG. 6 of the drawings is a top view of the fin member and needle hub of FIGS. 4 and 5.
Figure 5:
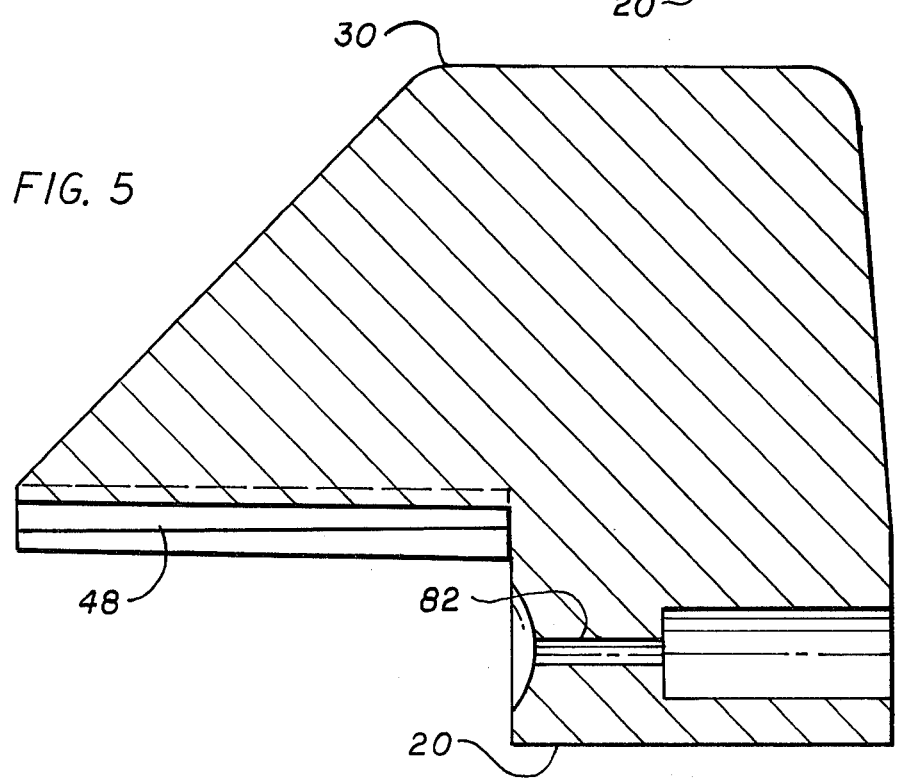
FIG. 5 of the drawings is a vertical section, taken along the midline of the needle hub and fin member of FIG. 4.

FIG. 4 of the drawings shows T-shaped track member 46 disposed vertically from catheter hub 14 and female track member 48 disposed proximally from needle hub 20. FIG. 5 of the drawings shows a modular needle hub 20 having fin member 30 extending vertically therefrom with female track member 48 integrally formed therein. Aperture 82 is also integrally formed therein and is designed for fixed attachment to needle 18 (not shown). FIG. 6 is a top view of needle hub 20 showing in particular upper substantially horizontal surface 40 disposed on fin 30 and rib members 54 disposed radially therefrom. In addition, as further shown in FIG. 6, in a preferred embodiment, surfaces 36 and 38 may be radially indented in order to improve gripability of fin member 30.

It should be noted that in an alternative embodiment of the invention, T-shaped track member 46 may extend along catheter hub 14 and a corresponding male track member (not shown) may also run along needle hub 20. A catheter clip 84 having aperture 52 running therethrough may be used to connect needle hub 20 to catheter hub 14. In order to separate needle hub 20 from catheter hub 14, catheter clip 84 may be slidably removed from male track member 46.

The foregoing description and drawings merely explain and illustrate the invention, and the invention is not limited thereto, except insofar as the appended claims are so limited as those skilled in the art who have the disclosure before them will be able to make modifications and variations therein without departing from the scope of the invention.

We claim:

1. An improved venipuncture device comprising:
    catheter means having catheter hub means attached thereto at a first end;
    needle means having needle hub means attached thereto at a first end and a sharpened tip at a second end, said needle means extending coaxially through said catheter means with said sharpened tip extending from said catheter means at a second end and being adapted for insertion and removal from said catheter means; and
    a fin member extending substantially vertically from said needle hub means and longitudinally along a substantial portion of the length of said catheter hub means whereby said device may be easily grasped, balanced and manipulated during venipuncture;
    guide track means longitudinally disposed along the exterior of said catheter hub, along the base portion of said fin member and along said needle hub, said guide track means being constructed and arranged for the slidable attachment or detachment of said needle hub means to said catheter hub means, said guide track means further being effective to prevent rotation of said needle means within said catheter means;
    said base portion of said fin member being disposed coaxially with and extending vertically from said guide track means so as to facilitate kinesthesis, ease of venipuncture, and joinder or separation of said catheter hub means from said needle hub means by means of said fin member.

2. The invention according to claim 1 in which said fin member comprises a pair of oppositely disposed substantially planer substantially vertical surfaces being constructed and arranged in both size and disposition relative to each other to be easily grasped between the thumb and index finger of the user.

3. The invention according to claim 1 in which the base portion of said fin member is positioned closely proximate to the axis of said needle means and is constructed and arranged for gripping thereby facilitating kinesthesis, manipulation of said device and ease of venipuncture.

4. The invention according to claim 1 in which said guide track means comprises;
    one or more male track members extending coaxially along said catheter hub; and
    one or more female track members extending proximally from said needle hub means, said female track members having an open lower portion and an aperture therethrough constructed and arranged for telescopic reception of and snugly fitting attachment to said male track member so as to join said catheter hub means to said needle hub means.

5. The invention according to claim 1 in which said fin member includes a plurality of vertical rib members integrally formed therein and uniformly arranged thereon and adapted for the strengthening of said fin member and for facilitating the gripping thereof.

6. The invention according to claim 1 in which said catheter hub means further includes a tab member extending from said catheter hub means constructed and arranged for the digital application of force thereon so as to facilitate separation of said needle means from said catheter means; said fin member including a substantially vertical forward surface constructed and arranged in relation to said tab member so as to allow ddigital access to said tab member, thereby permitting digital separation of said needle hub from said catheter hub.

7. The invention according to claim 1 in which said venipuncture device further comprises:
    a pair of oppositely extending flexible wing sections flexibly attached to said catheter hub means, said flexible wing sections each have an area of reduced thickness along a portion of the width thereof substantially adjacent to said catheter hub means, said area of reduced thickness being effective to facilitate the folding of said flexible wing sections together so as to be easily held thereby facilitating insertion of said device into the patient's vein.

8. The invention according to claim 1 in which said venipuncture device further includes:
    a wing hub member having an axial bore therethrough adapted for telescopic reception of and attachment to said catheter portion; and
    a pair of oppositely extending flexible wing sections flexibly attached to said wing hub member, said flexible wing sections having an area of reduced thickness on each of said flexible wing sections along a portion of the width thereof, substantially adjacent to said wing hub member, said area of reduced thickness being effective to facilitate the folding of said flexible wing sections together so as to be easily held thereby, facilitating insertion of said device into the patient's vein.

9. The invention according to claim 7 or 8 in which said fin member includes a substantially vertical forward surface constructed and arranged for digital separation of said needle hub means from said catheter hub means when said flexible wing sections are grasped and maintained in a stationary position.

10. The invention according to claim 7 in which said wing hub member further includes a tab member constructed and arranged for the digital application of force thereon so as to facilitate separation of said needle from said catheter means.

11. The invention according to claim 1 in which said catheter means further comprises an additive tubing port radially extending from said catheter hub means and adapted for connection to a length of flexible tubing.

12. The invention according to claim 11 in which said needle means further comprises a priming aperture integrally formed in said needle means, said priming aperture being positioned proximate said additive tubing port within said catheter hub means when said needle means is positioned within said catheter means whereby an intravenous solution may be introduced through said flexible tubing, into and through said additive tubing port, into and through said priming aperture and into and through said needle means so as to fill said needle with said solution and thereby prevent the passage of air bubbles into the vein of the patient.

13. The invention according to claim 1 in which said catheter hub means further includes a penetrable elastic sealing member contained therein, said needle means extending coaxially therethrough, said sealing member being constructed and arranged so as to hermetically seal said catheter hub upon insertion or removal of said needle means.

* * * * *

UNITED STATES PATENT AND TRADEMARK OFFICE
CERTIFICATE OF CORRECTION

PATENT NO. : 4,326,519
DATED : April 27, 1982
INVENTOR(S) : Herbert F. D'Alo, Andrew J. Muetterties It is certified that error appears in the above—identified patent and that said Letters Patent is hereby corrected as shown below:

In Column 8:

Claim 5, line 30, "arranged" should be "arrayed"

Signed and Sealed this

Seventh Day of September 1982

[SEAL]

Attest:

Attesting Officer

GERALD J. MOSSINGHOFF
Commissioner of Patents and Trademarks